(12) United States Patent
Mansson et al.

(10) Patent No.: US 9,573,001 B2
(45) Date of Patent: Feb. 21, 2017

(54) DEPILATORY COMPOSITION

(75) Inventors: Asa Mansson, Stockholm (SE); Candice Monge, East Yorkshire (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 0 days.

(21) Appl. No.: 13/132,585

(22) PCT Filed: Dec. 4, 2009

(86) PCT No.: PCT/GB2009/002817
§ 371 (c)(1),
(2), (4) Date: Jul. 14, 2011

(87) PCT Pub. No.: WO2010/064017
PCT Pub. Date: Jun. 10, 2010

(65) Prior Publication Data
US 2011/0302723 A1  Dec. 15, 2011

(30) Foreign Application Priority Data
Dec. 5, 2008  (GB) .................................. 0822257.2

(51) Int. Cl.
*A61K 36/00* (2006.01)
*A61Q 9/04* (2006.01)
*A61K 8/46* (2006.01)
*A61K 8/92* (2006.01)

(52) U.S. Cl.
CPC . *A61Q 9/04* (2013.01); *A61K 8/46* (2013.01); *A61K 8/922* (2013.01)

(58) Field of Classification Search
None
See application file for complete search history.

(56) References Cited

U.S. PATENT DOCUMENTS 2,487,558 A * 11/1949 Kamlet .................... A61K 8/23
                                                        8/161
2003/0118535 A1* 6/2003 Lustbader et al. ........... 424/70.1
2007/0298482 A1* 12/2007 Krishna et al. ............ 435/252.5

FOREIGN PATENT DOCUMENTS

DE       20204421 U1 *  6/2002 ............... A61K 8/19
JP       03115212 A  *  5/1991
WO    WO 2008/110745  *  9/2008

OTHER PUBLICATIONS

Yuzu from "Citrus Varieties", by College of Natural and Agricultural Science, accessed on Apr. 12, 2013, pp. 1-3.*

* cited by examiner

*Primary Examiner* — Qiuwen Mi
(74) *Attorney, Agent, or Firm* — Troutman Sanders LLP; Ryan A. Schneider; Chris N. Davis

(57) ABSTRACT

A depilatory cream composition comprising a depilatory active, and one or more volatile, essential oils selected from the group consisting of orange oil, cedarwood oil, patchouli oil, pine oil, cabreuva oil, guaiacwood oil, lavandin oil, bergamot oil, petitgrain paraguay oil, lavender oil, mint oil, Virginia cedarwood oil, *Citrus Aurantium dulcis* oil and *Citrus grandis* oil.

19 Claims, No Drawings

DEPILATORY COMPOSITION

CROSS-REFERENCE TO RELATED APPLICATIONS

This application is a US National Stage of International Application No. PCT/GB2009/002817, filed 4 Dec. 2009, which claims the benefit of GB 0822257.2, filed 5 Dec. 2008, both herein fully incorporated by reference.

FIELD OF THE INVENTION

The present invention relates to a depilatory cream composition. In particular, the present invention relates to a depilatory cream which has improved odour properties.

BACKGROUND OF THE INVENTION

Depilatory creams for removing unwanted hair are known. Such creams typically include a depilatory active that degrades hair keratin.

Typically, the active agent in depilatory creams is based on a sulphur-containing compound such as potassium thioglycolate. An unpleasant odour is commonly associated with this type of compound. The depilatory active achieves its effect by weakening the hair. In doing so the depilatory active acts as reducing which results in the production of volatile sulphur-containing compounds. These sulphur-containing compounds also have an unpleasant odour.

Furthermore, In use the depilation cream is applied to a user's skin and left for a period of up to 10 mins while the active achieves its effect.

It would, therefore, be desirable to use a depilatory cream which avoids the unpleasant odours of creams currently available.

BRIEF SUMMARY OF THE INVENTION

According to a first aspect of the present invention there is provided a depilatory cream composition comprising a depilatory active, and one or more volatile, essential oils.

According to a second aspect of the present invention, there is provided a method of depilation comprising:
a. applying a composition as defined above to the skin;
b. allowing the composition a residence time on the skin in order to degrade hairs on the skin's surface;
c. at the end of the residence time removing the composition and depilated hairs form the skin; and
d. rinsing the skin.

The one or more volatile, essential oils can be selected from the group consisting of orange oil, cedarwood oil, patchouli oil, pine oil, cabreuva oil, guaiacwood oil, lavandin oil, bergamot oil, petitgrain paraguay oil, lavender oil, mint oil, virginia cedarwood oil, *Citrus Aurantium dulcis* oil and *Citrus grandis* oil.

The depilatory composition may contain a skin-feel enhancing agent selected from at least one of silicone wax, talc and polyamide resin in the depilatory cream composition. In particular, the silicone wax, talc and/or a polyamide resin impart(s) a soft and velvety after-feel to the depilatory cream composition without affecting the composition's hair removal properties.

Talc is particularly preferred over other minerals which have previously been used in cosmetics as it confers a powdery after-feel which is desirable. In addition, it does not alter the colour of the composition. The talc may be present in an amount of 0.1 to 10 weight %, preferably 0.2 to 5 weight %, more preferably 0.5 to 3 weight %. In one embodiment, the composition includes 1 to 2 weight % talc.

The depilatory cream composition may further include a humectant. Suitable humectants include polyols, such as glycerine, propylene glycol and butylene glycol. Glycerine is preferred. The humectant may be present in an amount of 0 to 10 weight %, preferably 0.5 to 5 weight %.

The composition may comprise a polyamide resin as an alternative or in addition to the mineral. The polyamide resin may be present in an amount of 0.1 to 10 weight %, preferably 0.5 to 5 weight %, more preferably 1 to 3 weight %, for example 2 weight %. The polyamide resin is preferably Nylon-12.

The composition may also comprise a silicone wax as an alternative or in addition to the mineral and/or polyamide resin. Suitable silicone waxes include $C_{30}$-$C_{45}$ alkyl methicone and a silicone wax formed from stearoxytrimethylsilane and stearyl alcohol. The silicone wax is preferably $C_{30}$-$C_{45}$ alkyl methicone.

The silicone wax may be present in an amount of 0.1 to 10 weight %, preferably 0.5 to 5 weight %, more preferably 1 to 3 weight %, for example 1 to 2 weight %.

The emollient is selected from at least one of mineral oil, silicone and emollient esters. Together with the silicone wax, mineral and/or polyamide resin (and optional humectant), the emollient plays an important role in providing the depilatory cream composition with its desired skin-feel characteristics.

The emollient may be present in an amount of 1 to 10 weight %, preferably 3 to 7 weight % of the composition.

Mineral oil may be present in an amount of 0 to 10 weight %, preferably 0.5 to 5 weight % of the composition.

Silicone oil may be present in an amount of 0 to 10 weight %, preferably 0.5 to 5 weight %, for example 1 to 4 weight % of the composition.

Emollient esters may be present in an amount of 0 to 10 weight %, preferably 0.5 to 5 weight % of the composition, for example 1 to 3 weight %.

It is possible for the emollient to consist essentially of mineral oil. For example, in one embodiment, the composition includes talc and an emollient that consists essentially of mineral oil. In this embodiment, the emollient is present in an amount of 3 to 6 weight %, preferably 5 weight %. The talc is present in an amount of 0.3 to 1 weight %, preferably 0.5 weight %. Where an emollient consisting essentially of mineral oil emollient is employed, the composition preferably includes a humectant, such as glycerine.

It is also possible for the emollient to comprise or consist essentially of silicone oil(s). Preferably, a combination of silicone oils are present. The silicone oil may include at least one of cyclopentasiloxane, dimethiconol and dimethicone. Preferably, the silicone oil comprises cyclopentasiloxane, dimethiconol and dimethicone. The silicone oil may include 0.1 to 5 weight %, preferably 1 to 2 weight % dimethicone; and/or 1 to 5 weight %, for example, 1 to 3 weight % cyclopentasiloxane and dimethiconol.

It is possible for the emollient to consist essentially of an emollient ester. However, the emollient ester is preferably used in combination with a mineral oil and/or a silicone oil.

In one embodiment, the emollient comprises at least two of mineral oil, silicone oil and emollient esters. For example, the emollient may include mineral oil and silicone oil, or mineral oil and emollient esters, or silicone oil and emollient esters. In one embodiment, the emollient includes mineral oil, silicone oil and emollient esters.

Any suitable silicone oil may be employed. Examples include cyclopentasiloxane, dimethiconol and dimethicone. The total amount of silicone oil in the composition may be 0.1 to 10 weight %, for example, 2 to 5 weight %.

Any suitable emollient ester may be employed. Suitable examples include isopropyl palmitate, isopropyl myristate, myristyl lactate, cetyl esters, isotridecyl isononanoate, $C_{12-15}$ alkyl benzoate, caprylic/capric triglyceride and pentaerythrityl tetraisostearate.

In one embodiment, the emollient comprises mineral oil. The mineral oil may be present in an amount of 3 to 6 weight %, preferably 5 weight %. In a preferred embodiment, this combination of emollients is used together with at least one of talc and polyamide resin.

The depilatory active is a compound capable of degrading keratin and may be, for example, a sulphur compound such as potassium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, MgS, CaS, SrS, BaS, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptropropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and/or cysteamine. However, the composition is preferably substantially or, more preferably, is completely free from depilatory agents that destroy the thermodynamic equilibrium or the surface tension of the composition; examples of such agents include alkali metal sulphides.

Preferred depilatory compounds are thioglycolates, or their precursor thioglycolic acid. Most preferred is potassium thioglycolate, which may be produced by mixing thioglycolic acid with a neutralising source of potassium hydroxide (as noted above excess potassium hydroxide over that required to effect neutralisation cannot be used).

The depilatory active may be present in an amount of 2 to 25 weight %, preferably 5 to 20 weight %, more preferably 10 to 15 weight %. In one embodiment, the composition includes potassium thioglycolate in an amount of 2 to 25 weight %, preferably 5 to 20 weight %, more preferably 10 to 15 weight %.

The depilatory cream composition of the present invention preferably includes water. Water may be present in an amount of at least 40 weight %, preferably at least 50 weight %. Suitable amounts of water range from 40 to 70 weight %, preferably 50 to 65 weight %, more preferably 55 to 60 weight %.

The depilatory cream composition may optionally include one or more surfactant(s). The surfactant may be anionic, cationic or non-ionic. It is preferably non-ionic. Examples of suitable surfactants include cetearyl phosphate, cetearyl alcohol, cetearyl glucoside, cetostearyl alcohol and/or ceteareth 20. It is preferably present in an amount of from 0.5 to 15 wt % relative to the weight of the depilatory cream composition, more preferably from 1 to 10 wt %.

The depilatory cream composition may optionally include a source of alkalinity. This may include hydroxides, such as hydroxides of alkali and alkaline earth metals. Suitable hydroxides include sodium hydroxide, potassium hydroxide, calcium hydroxide and magnesium hydroxide. Preferably, calcium hydroxide is employed, optionally together with potassium hydroxide. The source of alkalinity (e.g. calcium hydroxide) may be present in an amount of 0.1 to 10 weight %, preferably 1 to 6 weight %, for example 2 to 5 weight % of the depilatory cream composition.

The depilatory cream composition preferably has a pH of greater than 7, for example, 9 to 12.5.

Optionally, the composition includes an accelerator that will accelerate the hair removal reaction. Examples of such accelerators include urea, thiourea, dimethyl, isosorbide (DMI), ethoxydiglycol (Transcutol) or methyl propyl diol (MP diol). Preferably the accelerator is urea. The composition according to the invention preferably comprises from 5% to 15% wt, more preferably from 6 to 10 wt % of an accelerator (e.g. urea).

The depilatory cream composition may comprise other optional ingredients, such as pigments and fillers, such as clays. Examples of suitable clays include sodium magnesium silicate, magnesium trisilicate and titanium dioxide. The inclusion of a clay, preferably sodium magnesium silicate, more preferably in an amount of from 0.1 to 10 wt % relative to the weight of the depilatory composition, most preferably from 0.1 to 1 wt %, is particularly advantageous, since this provides sodium and magnesium ions for the buffer system and improves the efficiency of depilation.

The depilatory cream composition desirably includes a chelating agent, such as sodium gluconate. The chelating agent may be present in an amount of less than 1 weight %, preferably 0.01 to 0.5 weight %, for example 0.05 to 0.1 weight %.

The depilatory cream composition may also include an additive that prevents phase separation. Suitable additives include polymers or copolymers of acrylic acid, for example, an acrylate copolymer. Such additives may be present in an amount of up to 2 weight %, preferably less than 1 weight %, more preferably less than 0.5 weight %, for example 0.1 to 0.4 weight %.

Optionally, additives such as aloe vera and Vitamin E may also be included in the composition. Such additives are employed in amounts of less than 1 weight %, for example, 0.1 to 0.5 weight % of the composition.

The composition can be in the form of a base cream, an aerosol cream or a shower cream.

In the method of depilation of the present invention the composition is allowed a residence time on the skin. Preferably the residence time is less than 10 minutes, more preferably not more than 6 minutes, even. Very suitably the residence time is 1 to 5 minutes, about 2 to 3 minutes being especially preferred.

It is found that using the composition of the present invention depilation after a residence time of only 3 minutes can be excellent, yet without significant skin irritation in subjects with normal skin.

DETAILED DESCRIPTION OF PREFERRED EMBODIMENTS

The composition may be removed from the skin by any means, for example using a sponge, spatula or scraper device.

The following Examples further illustrate the present invention.

| Component | Ex. 1 (Wt %) | Ex. 2 (Wt %) | Ex. 3 (Wt %) | Ex. 4 (Wt %) |
|---|---|---|---|---|
| Deionised Water | 57.995 | 57.995 | 57.995 | 57.995 |
| Urea | 8.00 | 8.00 | 8.00 | 8.00 |
| Paraffinum Liquidum | 5.00 | 5.00 | 5.00 | 5.00 |
| Cetearyl alcohol 30/70 | 4.40 | 4.40 | 4.40 | 4.40 |
| Potassium thioglycolate | 12.90 | 12.90 | 12.90 | 12.90 |
| Calcium hydroxide | 3.56 | 3.56 | 3.56 | 3.56 |
| Talc | 2.00 | 2.00 | 2.00 | 2.00 |
| Ceteareth-20 | 1.76 | 1.76 | 1.76 | 1.76 |
| Glycerin | 1.00 | 1.00 | 1.00 | 1.00 |
| Potassium hydroxide | 1.00 | 1.00 | 1.00 | 1.00 |
| Magnesium trisilicate | 0.50 | 0.50 | 0.50 | 0.50 |
| Titanium dioxide | 0.3303 | 0.3303 | 0.3303 | 0.3303 |
| Propylene glycol | 0.2667 | 0.2667 | 0.2667 | 0.2667 |
| Li Mg silicate | 0.20 | 0.20 | 0.20 | 0.20 |
| Sodium gluconate | 0.10 | 0.10 | 0.10 | 0.10 |
| Acrylates copolymer 33 | 0.10 | 0.10 | 0.10 | 0.10 |
| Hydrated silica | 0.025 | 0.025 | 0.025 | 0.025 |
| CI 77289 | | | | |
| Simmondsia Chinensis Seed Oil | | | | |
| Aloe barbadensis leaf extract | | | | |
| Lotus flower milk | 0.100 | 0.10 | 0.10 | 0.10 |
| Shea butter | 0.100 | 0.10 | 0.10 | 0.10 |
| CI45380:3 | 0.003 | 0.003 | 0.003 | 0.003 |
| Sweet almond oil | | | | |
| Cotton extract | | | | |
| Parfum/Fragrance BN1/886/00 (no essential oils) | 0.56 | | | |
| Parfum/Fragrance OM 59130 (no essential oils) | | 0.56 | | |
| Parfum/Fragrance OM 59131 (no essential oils) | | | 0.56 | |
| Parfum (contains: Orange Oil 0.1-0.5%, Cedarwood Oil 1-5%) | | | | 0.56 |
| Citrus Aurantium dulcis oil, Limonene | 0.05 | 0.05 | 0.05 | 0.05 |
| Citrus grandis oil, Limonene | 0.05 | 0.05 | 0.05 | 0.05 |

| Component | Ex. 5 (Wt %) | Ex. 6 (Wt %) | Ex. 7 (Wt %) | Ex. 8 (wt %) |
|---|---|---|---|---|
| Deionised Water | 57.995 | 57.995 | 62.34 | 62.34 |
| Urea | 8.00 | 8.00 | 8.00 | 8.00 |
| Paraffinum Liquidum | 5.00 | 5.00 | 5.00 | 5.00 |
| Cetearyl alcohol 30/70 | 4.40 | 4.40 | 4.40 | 4.40 |
| Potassium thioglycolate | 12.90 | 12.90 | 10.00 | 10.00 |
| Calcium hydroxide | 3.56 | 3.56 | 3.20 | 3.20 |
| Talc | 2.00 | 2.00 | 2.00 | 2.00 |
| Ceteareth-20 | 1.76 | 1.76 | 1.76 | 1.76 |
| Glycerin | 1.00 | 1.00 | 1.00 | 1.00 |
| Potassium hydroxide | 1.00 | 1.00 | | |
| Magnesium trisilicate | 0.50 | 0.50 | 0.50 | 0.50 |
| Titanium dioxide | 0.308 | 0.308 | 0.3333 | 0.3333 |
| Propylene glycol | 0.2667 | 0.2667 | 0.2667 | 0.2667 |
| Li Mg silicate | 0.20 | 0.20 | 0.20 | 0.20 |
| Sodium gluconate | 0.10 | 0.10 | 0.10 | 0.10 |
| Acrylates copolymer 33 | 0.10 | 0.10 | 0.10 | 0.10 |
| Hydrated silica | 0.025 | 0.025 | | |
| CI 77289 | 0.0253 | 0.0253 | | |
| Simmondsia Chinensis Seed Oil | 0.10 | 0.10 | | |
| Aloe barbadensis leaf extract | 0.10 | 0.10 | | |
| Lotus flower milk | | | | |
| Shea butter | | | | |
| CI45380:3 | | | | |
| Sweet almond oil | | | 0.10 | 0.10 |
| Cotton extract | | | 0.10 | 0.10 |
| Parfum/Fragrance BD1/294/00 (no essential oils) | 0.56 | | | |
| Parfum/Fragrance BS1/603/00 (no essential oils) | | | | 0.5 |
| Parfum/Fragrance BS1/499/00 (contains: Sweet Almond Oil 45-50%, Orange Oil 0.1-0.5%, Clove Oil 0.05-0.1%, Eucalyptus Oil 0.05-0.1%, Pine Oil 0.01-0.05%, Cocoa Oil 0.01-0.05%) | | 0.56 | 0.5 | |
| Citrus Aurantium dulcis oil, Limonene | 0.05 | 0.05 | 0.05 | 0.05 |
| Citrus grandis oil, Limonene | 0.05 | 0.05 | 0.05 | 0.05 |

| Component | Ex. 9 (Wt %) | Ex. 10 (Wt %) | Ex. 11 (Wt %) | Ex. 12 (wt %) |
|---|---|---|---|---|
| Deionised Water | 57.995 | 57.995 | 62.34 | 62.34 |
| Urea | 8.00 | 8.00 | 8.00 | 8.00 |
| Paraffinum Liquidum | 5.00 | 5.00 | 5.00 | 5.00 |
| Cetearyl alcohol 30/70 | 4.40 | 4.40 | 4.40 | 4.40 |
| Potassium thioglycolate | 12.90 | 12.90 | 10.00 | 10.00 |
| Calcium hydroxide | 3.56 | 3.56 | 3.20 | 3.20 |
| Talc | 2.00 | 2.00 | 2.00 | 2.00 |
| Ceteareth-20 | 1.76 | 1.76 | 1.76 | 1.76 |
| Glycerin | 1.00 | 1.00 | 1.00 | 1.00 |
| Potassium hydroxide | 1.00 | 1.00 | | |
| Magnesium trisilicate | 0.50 | 0.50 | 0.50 | 0.50 |
| Titanium dioxide | 0.308 | 0.3303 | 0.3333 | 0.3333 |
| Propylene glycol | 0.2667 | 0.2667 | 0.2667 | 0.2667 |
| Li Mg silicate | 0.20 | 0.20 | 0.20 | 0.20 |
| Sodium gluconate | 0.10 | 0.10 | 0.10 | 0.10 |
| Acrylates copolymer 33 | 0.10 | 0.10 | 0.10 | 0.10 |
| Hydrated silica | 0.025 | 0.025 | | |
| CI 77289 | 0.0253 | | | |
| Simmondsia Chinensis Seed Oil | 0.10 | | | |
| Aloe barbadensis leaf extract | 0.10 | | | |
| Lotus flower milk | | 0.10 | | |
| Shea butter | | 0.10 | | |
| CI45380:3 | | 0.0030 | | |
| Sweet almond oil | | | 0.10 | 0.10 |
| Cotton extract | | | 0.10 | 0.10 |
| parfum, benzyl salicylate, butylphenyl Methylpropional, Linalool | 0.56 | | | |
| parfum, butylphenyl methylpropional, citronellol, limonene (contains: Orange Oil 15-20%, Cedarwood Oil 1-5%, Patchouli Oil 0.1-0.5%, Pine Oil 0.05-0.1%) | | 0.66 | | |
| parfum, Limonene (contains: Cabreuva Oil 10-15%, Cedarwood Oil 1-5%, Guaiacwood Oil 1-5%, Orange Oil 1-5%, Lavandin Oil 0.1-0.5%) | | | 0.60 | |
| Parfum, Linalool, Limonene (contains: Bergamot Oil, Orange Oil, Petitgrain Paraguay Oil, Lavender Oil, Mint Oil, Virginia Cedarwood Oil) | | | | 0.60 |
| Citrus Aurantium dulcis oil, Limonene | 0.05 | | | |

| | |
|---|---|
| *Citrus grandis* oil, Limonene | 0.05 |

The compositions can be formulated using standard techniques known to the man skilled in the art.

An advantage of the composition of the present invention is that there is provided a composition which reduces the unpleasant malodour experienced by an individual when using currently available compositions. The malodour score for the example embodiments described previously is given below.

| Example | Malodour score |
|---|---|
| 1 | 3.17 |
| 2 | 3.42 |
| 3 | 3.83 |
| 4 | 2.13 |
| 5 | 3.6 |
| 6 | 2.32 |
| 7 | 3.12 |
| 8 | 4 |

Known compositions typically have a malodour score of greater than 4. For example, the formulation given below has a score of 4.

| Component | Wt % |
|---|---|
| Deionised Water | 58.095 |
| Urea | 8.00 |
| Paraffinum Liquidum | 5.00 |
| Cetearyl alcohol 30/70 | 4.40 |
| Potassium thioglycolate | 12.90 |
| Calcium hydroxide | 3.56 |
| Talc | 2.00 |
| Ceteareth-20 | 1.76 |
| Glycerin | 1.00 |
| Potassium hydroxide | 1.00 |
| Magnesium trisilicate | 0.50 |
| Titanium dioxide | 0.3303 |
| Propylene glycol | 0.2667 |
| Li Mg silicate | 0.20 |
| Sodium gluconate | 0.10 |
| Acrylates copolymer 33 | 0.10 |
| Hydrated silica | 0.025 |
| Lotus flower milk | 0.100 |
| Shea butter | 0.100 |
| CI45380:3 | 0.003 |
| Parfum/Fragrance Thelma 200 (no essential oils) | 0.56 |

Further modifications and improvements can be incorporated without departing from the scope of the invention disclosed herein.

The invention claimed is:

1. A depilatory cream composition comprising:
a depilatory active selected from the group consisting of potassium thioglycolate, dithioerythritol, thioglycerol, thioglycol, thioxanthine, thiosalicylic acid, N-acetyl-L-cysteine, lipic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, NaSH, KSH, thioglycolic acid, 2-mercaptopropionic acid, 3-mercaptopropionic acid, thiomalic acid, ammonium thioglycolate, glyceryl monothioglycolate, monoethanolamine thioglycolate, monoethanolamine, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, thioglycolhydrazine, keratinase, hydrazine sulphate, hydrazine disulphate, triisocyanate, guanidine thioglycolate, calcium thioglycolate and cysteamine; and
one or more volatile, essential oils selected from the group consisting of *Citrus Aurantium dulcis* oil and *Citrus grandis* oil;
wherein the depilatory cream composition comprises 0.05 to 0.1 weight % volatile, essential oil; and
wherein the depilatory cream composition has reduced malodour.

2. The composition as claimed in claim 1, wherein the composition further comprises a skin-enhancing agent.

3. The composition as claimed in claim 2 wherein the skin-enhancing agent is a talc.

4. The composition as claimed in claim 1, further comprising a humectant.

5. The composition as claimed in claim 4, wherein the humectant is glycerine.

6. The composition as claimed in claim 1, comprising 2 to 20 weight % depilatory active.

7. The composition as claimed in claim 6 wherein the depilatory active is potassium thioglycolate.

8. The composition as claimed in claim 1, further comprising 1 to 10 weight % emollient.

9. The composition as claimed in claim 8 wherein the emollient is mineral oil.

10. A method of depilation comprising:
applying the composition of claim 1 to skin;
allowing the composition a residence time on the skin in order to degrade hairs on the skin's surface;
at the end of the residence time removing at least a portion of the composition and depilated hairs from the skin; and
rinsing the skin.

11. The method of depilation according to claim 10, wherein the one or more volatile, essential oils reduces the production of volatile sulphur-containing compounds.

12. In a method of depilation producing unpleasant malodor when using a conventional depilatory cream comprising (i) applying the conventional depilatory cream to skin, (ii) allowing the cream a residence time on the skin in order to degrade hairs on the skin's surface, (iii) at the end of the residence time removing at least a portion of the cream and depilated hairs form the skin, and (iv) rinsing the skin, the improvement comprising the step of reducing the unpleasant malodor when using the conventional depilatory cream by replacing the conventional depilatory cream with the cream composition of claim 1, wherein the one or more volatile, essential oils of the cream composition of claim 1 reduces the unpleasant malodour produced with use of the conventional depilatory cream.

13. The method of depilation according to claim 12, wherein the composition comprises 0.05 weight % volatile, essential oil.

14. The method of depilation according to claim 12, wherein the composition further comprises a skin-enhancing agent.

15. The method of depilation according to claim 14, wherein the skin-enhancing agent is a talc.

16. The method of depilation according to claim 12, wherein the composition further comprises a humectant.

17. The method of depilation according to claim 16, wherein the humectant is glycerine.

18. The method of depilation according to claim 12, wherein the composition comprises 2 to 20 weight % depilatory active.

19. The method of depilation according to claim 12, wherein the depilatory active is potassium thioglycolate.

* * * * *